(12) United States Patent
Kakee

(10) Patent No.: US 8,926,512 B2
(45) Date of Patent: Jan. 6, 2015

(54) ULTRASONIC IMAGING APPARATUS AND ULTRASONIC VELOCITY OPTIMIZATION METHOD

(75) Inventor: Akihiro Kakee, Nasushiobara (JP)

(73) Assignees: Kabushiki Kaisha Toshiba, Tokyo (JP); Toshiba Medical Systems Corporation, Otaware-shi (JP)

( * ) Notice: Subject to any disclaimer, the term of this patent is extended or adjusted under 35 U.S.C. 154(b) by 815 days.

(21) Appl. No.: 12/056,596

(22) Filed: Mar. 27, 2008

(65) Prior Publication Data
US 2008/0242999 A1 Oct. 2, 2008

(30) Foreign Application Priority Data
Mar. 28, 2007 (JP) ................................. 2007-085918

(51) Int. Cl.
*A61B 8/14* (2006.01)
*A61B 8/00* (2006.01)
*G01S 15/89* (2006.01)
*G01S 7/52* (2006.01)

(52) U.S. Cl.
CPC .............. *A61B 8/00* (2013.01); *G01S 15/8979* (2013.01); *A61B 8/54* (2013.01); *G01S 7/52049* (2013.01); *G01S 7/52046* (2013.01)
USPC ............ 600/443; 600/449; 600/455; 600/459

(58) Field of Classification Search
CPC ........ A61B 8/54; A61B 8/06; G01S 7/52049; G01S 7/52073; G01S 7/52074
USPC .......... 600/437, 447, 453, 455; 382/128, 130, 382/131
See application file for complete search history.

(56) References Cited

U.S. PATENT DOCUMENTS

| 5,415,173 | A | * | 5/1995 | Miwa et al. | 600/447 |
| 5,638,820 | A | * | 6/1997 | Chen et al. | 600/437 |
| 5,971,927 | A | * | 10/1999 | Mine | 600/455 |
| 6,305,225 | B1 | * | 10/2001 | Bae et al. | 73/602 |
| 7,513,872 | B2 | * | 4/2009 | Baba et al. | 600/455 |
| 7,666,142 | B2 | * | 2/2010 | Uchibori | 600/453 |

(Continued)

FOREIGN PATENT DOCUMENTS

| EP | 0 421 279 A1 | 4/1991 |
| JP | 3-176040 A | 7/1991 |

(Continued)

OTHER PUBLICATIONS

U.S. Appl. No. 12/249,309, filed Oct. 10, 2008, Nakaya, et al.

(Continued)

*Primary Examiner* — Baisakhi Roy
(74) *Attorney, Agent, or Firm* — Oblon, Spivak, McClelland, Maier & Neustadt, L.L.P.

(57) ABSTRACT

A resolution optimization unit determines an optimal sound velocity corresponding to a tissue component at each position in a scan slice, and calculates a reception delay time or the like for each reception beam from each position in the scan slice. A control processor executes delay addition processing in a scan for acquiring an ultrasonic image actually used for diagnosis by using the reception delay time calculated using an optimal sound velocity. This can correct the difference between the set sound velocity used for the calculation of a reception delay time and the actual in vivo sound velocity and acquire an ultrasonic image with optimized resolution.

26 Claims, 10 Drawing Sheets

(56) References Cited

U.S. PATENT DOCUMENTS

| | | | |
|---|---|---|---|
| 8,475,381 B2* | 7/2013 | Kakee et al. | 600/443 |
| 2003/0092990 A1* | 5/2003 | Baba et al. | 600/443 |
| 2009/0099451 A1* | 4/2009 | Nakaya et al. | 600/443 |
| 2010/0331692 A1* | 12/2010 | Kakee et al. | 600/443 |

FOREIGN PATENT DOCUMENTS

| | | |
|---|---|---|
| JP | 5-329159 | 12/1993 |
| JP | 6-304172 A | 11/1994 |
| JP | 7-116162 A | 5/1995 |
| JP | 2001-252276 A | 9/2001 |
| JP | 2005-536269 A | 12/2005 |
| JP | 2007-7045 | 1/2007 |
| JP | 2008-264531 | 11/2008 |

OTHER PUBLICATIONS

U.S. Appl. No. 12/824,697, filed Jun. 28, 2010, Kakee, et al.
Japanese Office Action Issued Dec. 4, 2012 in Patent Application No. 2008-088625 (with English translation).
Office Action issued Aug. 20, 2013, in Japanese Patent Application No. 2008-088625 with English translation.
Office Action issued Apr. 22, 2014 in Japanese Patent Application No. 2013-019952 (with English translation).

* cited by examiner

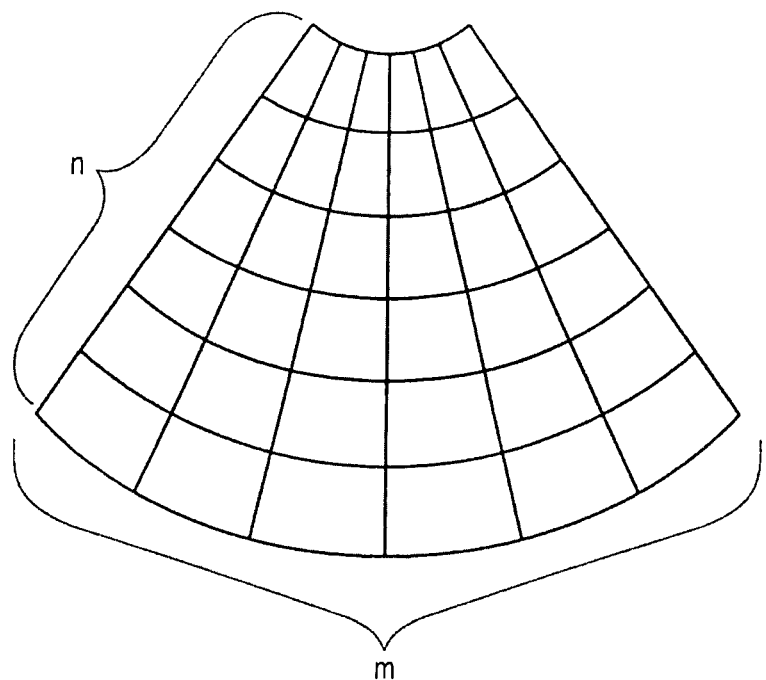
F I G. 4
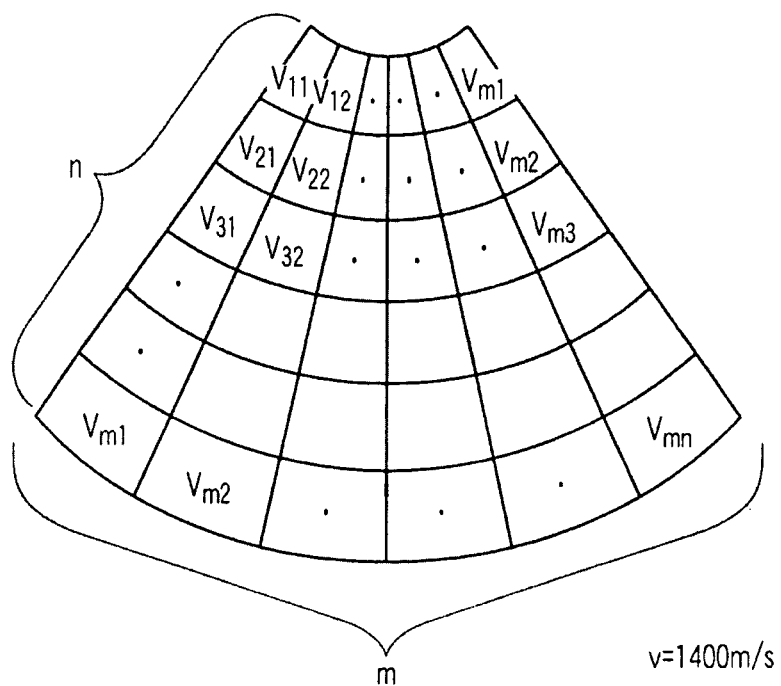
v=1400m/s
F I G. 5

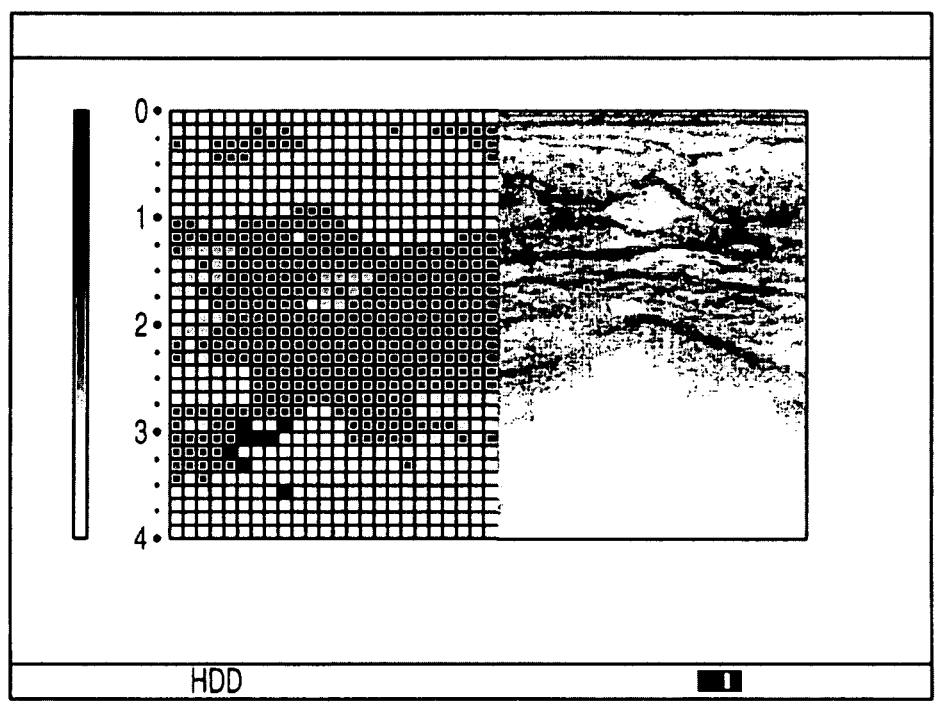
F I G. 11

(a)          (b)

ULTRASONIC IMAGING APPARATUS AND ULTRASONIC VELOCITY OPTIMIZATION METHOD

CROSS-REFERENCE TO RELATED APPLICATIONS

This application is based upon and claims the benefit of priority from prior Japanese Patent Application No. 2007-085918, filed Mar. 28, 2007, the entire contents of which are incorporated herein by reference.

BACKGROUND OF THE INVENTION

1. Field of the Invention

The present invention relates to an ultrasonic imaging apparatus and ultrasonic velocity optimization method which can automatically optimize a sound velocity in ultrasonic imaging used for image diagnosis, nondestructive inspection, or the like.

2. Description of the Related Art

Examples of an ultrasonic imaging apparatus which performs imaging by using ultrasonic waves include an ultrasonic inspection apparatus for nondestructively inspecting abnormality in a structure and an ultrasonic diagnosis apparatus which transmits ultrasonic waves to a subject (patient) and acquires tomograms associated with a diagnosis region on the basis of the reflected waves. For example, an ultrasonic diagnosis apparatus can display, in real time, how a heart beats or a fetus moves, with simple operation of bringing an ultrasonic probe into contact with the body surface. In addition, this apparatus offers a high level of safety, and hence can be repeatedly used for examination. Furthermore, the system size is smaller than those of other diagnosis apparatuses such as X-ray, CT, and MRI apparatuses. Therefore, this apparatus allows easy examination upon being moved to a bed side. That is, the apparatus is a convenient diagnosis technique. Ultrasonic diagnosis apparatuses used in such ultrasonic diagnosis vary depending on the types of functions which they have. Some compact apparatuses which can be carried with one hand have been developed. Ultrasonic diagnosis is free from the influence of radiation exposure such as X-ray exposure, and hence can be used in obstetric treatment, treatment at home, and the like.

An ultrasonic imaging apparatus typified by such an ultrasonic diagnosis apparatus uses a method of converging transmission and reception beams to improve the azimuth resolution of an image. Electronic scanning type array transducers, in particular, use an electronic convergence method based on delay time control for transmission/reception signals of each channel. A problem in this electronic convergence method is that a beam diverges at a place (depth) apart from a convergence point, and the azimuth resolution decreases.

For this problem, a conventional ultrasonic imaging apparatus uses a technique called a dynamic convergence method. This technique performs delay time control to continuously move a convergence point in the depth direction with a lapse of time at the time of reception. This technique allows to always acquire a reception ultrasonic beam from a converged area.

FIG. 13 is a view showing the positional relationship between each ultrasonic transducer of an ultrasonic probe and a focal point P in a subject to be examined. As shown in FIG. 13, letting X be the coordinates of the focal point P in the depth direction, and Yi be the coordinates of an ultrasonic transducer Ti in the array direction from the aperture center (origin O) of the ultrasonic probe, a delay time $\Delta ti$ from the time when the wavefront of a reflected sound wave reaches the aperture center to the time when the wavefront reaches the ultrasonic transducer Ti is given by $$\Delta ti = [(X^2 + Yi^2)^{1/2} - X]/C$$

where C is a sound velocity.

In this calculation, if the sound velocity used for the calculation is equal to the actual sound velocity of propagation in the subject, as shown in FIG. 14A, desired positions Fn−1, Fn, and Fn+1 can be made to coincide with the beam convergence point, thereby acquiring a high-resolution ultrasonic image.

A conventional ultrasonic diagnosis apparatus, however, calculates the delay time $\Delta ti$ by using a preset velocity (representative velocity) v representing a visualization target slice regardless of the position of the slice and the components of a progation medium, and sets the calculated time. The actual sound velocity of propagation in the subject does not always coincide with the representative velocity v. If, for example, the representative sound velocity used for calculation is lower than the actual sound velocity of propagation in the subject, as shown in FIG. 14B, a beam convergence point is located before the desired positions Fn−1, Fn, and Fn+1, resulting in a low resolution as compared with the case shown in FIG. 14A.

It has recently been reported that C=1560 cm/s in the muscle, and C=1480 cm/s in the fat. In addition, the sound velocity varies in individuals. The difference between the representative sound velocity v and the actual sound velocity of propagation C causes the difference between the assumed position of a convergence point and the actual position of the convergence point, resulting in image degradation.

As techniques for solving the difference between the assumed position of a convergence point and the actual position of the convergence point in a conventional ultrasonic diagnosis apparatus, techniques such as phase correction techniques based on a reflection method and a cross-correlation method are available. These techniques, however, require the presence of a reflector such as a calculus or a boundary wall, and has limitations such as the necessity of the presence of a reflector as a point. Even if, therefore, these techniques are used, it is impossible to acquire good images as a whole.

BRIEF SUMMARY OF THE INVENTION

The present invention has been made in consideration of the above situation, and has as its object to provide an ultrasonic imaging apparatus and ultrasonic velocity optimization method which can acquire ultrasonic images higher in resolution than that in the prior art by optimizing a sound velocity used for delay time calculation in ultrasonic imaging.

According to an aspect of the present invention, there is provided an ultrasonic imaging apparatus comprising a storage unit which stores a plurality of ultrasonic data acquired by using reception delay addition processing, based on different sound velocities, for a visualization target slice of a subject, a contrast value acquisition unit which segments each ultrasonic data into a plurality of small areas and acquires a contrast value for each of different sound velocities for each of the small areas, and a determination unit which determines an optimal sound velocity in execution of an ultrasonic scan on the visualization target slice by using a contrast value for each of different sound velocities for each small area.

According to another aspect of the present invention, there is provided an ultrasonic velocity optimization method comprising segmenting a plurality of ultrasonic data acquired by using reception delay addition processing, based on different sound velocities, for a visualization target slice of a subject into a plurality of small areas, acquiring a contrast value for each of different sound velocities for each small area, and determining an optimal sound velocity in execution of an ultrasonic scan on the visualization target slice by using a contrast value for each of different sound velocities for each small area.

BRIEF DESCRIPTION OF THE SEVERAL VIEWS OF THE DRAWING

FIG. 4 is a view showing a visualization target slice segmented into m×n small areas;

FIG. 5 is a view showing an example of a contrast value distribution map indicating the distribution of contrast values in the respective areas in the visualization target slice;

FIG. 11 is a view showing an example of the display form of a color sound velocity map;

DETAILED DESCRIPTION OF THE INVENTION

Figure 1:
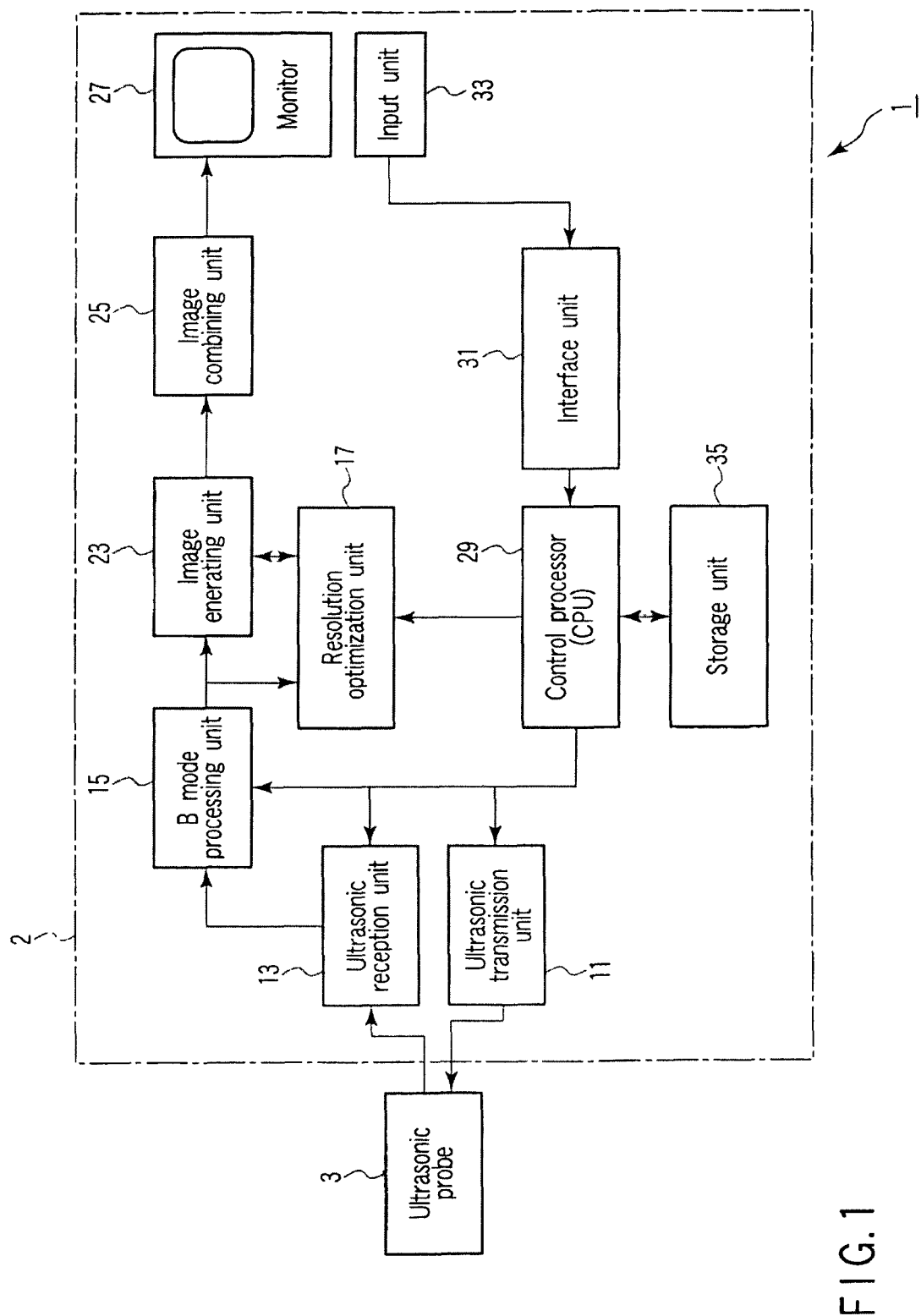
FIG. 1 is a block diagram showing the arrangement of an ultrasonic diagnosis apparatus 1 according to an embodiment.

The embodiments of the present invention will be described below with reference to the views of the accompanying drawing. Note that the same reference numerals denote constituent elements having substantially the same functions and arrangements, and a repetitive description will be made only when required. This embodiment exemplifies a case in which the technical idea of the present invention is applied to an ultrasonic diagnosis apparatus as an ultrasonic imaging apparatus. However, the technical idea of the present invention is not limited to this, and can be applied to, for example, an ultrasonic inspection apparatus used for nondestructive inspection and the like.

FIG. 1 is a block diagram showing the arrangement of an ultrasonic diagnosis apparatus 1 according to this embodiment. The ultrasonic diagnosis apparatus 1 comprises an apparatus body 2 and an ultrasonic probe 3. The apparatus body 2 comprises an ultrasonic transmission unit 11, an ultrasonic reception unit 13, a B mode processing unit 15, a resolution optimization unit 17, an image generating unit 23, an image combining unit 25, a monitor 27, a control processor (CPU) 29, an interface unit 31, an input unit 33, and a storage unit 35.

The ultrasonic probe 3 includes a plurality of piezoelectric transducers which generate ultrasonic waves on the basis of driving signals from the apparatus body 2 and convert reflected waves from a subject to be examined into electrical signals, a matching layer provided for the piezoelectric transducers, a backing member which prevents ultrasonic waves from propagating backward from the piezoelectric transducers, and the like. When an ultrasonic wave is transmitted from the ultrasonic probe 3 to a subject P to be examined, the transmitted ultrasonic wave is sequentially reflected by a discontinuity surface of acoustic impedance of internal body tissue, and is received as an echo signal by the ultrasonic probe 3. The amplitude of this echo signal depends on an acoustic impedance difference on the discontinuity surface by which the echo signal is reflected. The echo produced when an ultrasonic pulse is reflected by the surface of a moving blood flow, cardiac wall, or the like is subjected to a frequency shift depending on the velocity component of the moving body in the ultrasonic transmission direction due to a Doppler effect.

Note that the ultrasonic probe 3 can perform ultrasonic scanning on a three-dimensional area of a subject. In this case, the ultrasonic probe 3 has, for example, an arrangement designed to perform ultrasonic scanning on a three-dimensional area by mechanically swinging transducers along a direction perpendicular to the array direction of the transducers or an arrangement designed to perform ultrasonic scanning on a three-dimensional area by electrical control using two-dimensional vibration elements arrayed two-dimensionally. When the ultrasonic probe 3 has the former arrangement, three-dimensional scanning on the subject is performed by the swinging circuit. An examiner can therefore automatically acquire a plurality of two-dimensional tomograms by only bringing the probe body into contact with the subject. It is also possible to detect the accurate distance between slices from a controlled swinging velocity. When the ultrasonic probe 3 has the latter arrangement, it is possible in theory to perform ultrasonic scanning on a three-dimensional area in the same time as that required to acquire a conventional two-dimensional tomogram.

The ultrasonic transmission unit 11 has a trigger generating circuit, delay circuit, pulser circuit, and the like (none are shown). The pulser circuit repeatedly generates rate pulses for the formation of transmission ultrasonic waves at a predetermined rate frequency fr Hz (period: 1/fr sec). The delay circuit gives each rate pulse the delay time required to focus an ultrasonic wave into a beam for each channel and determine a transmission directivity. The trigger generating circuit applies a driving pulse to the probe 3 at the timing based on this rate pulse.

The ultrasonic reception unit 13 has an amplifier circuit, A/D converter, adder, and the like (none are shown). The amplifier circuit amplifies echo signals received through the ultrasonic probe 3 on a channel basis. The A/D converter gives each amplified echo signal the delay time required to determine a reception directivity. The adder then performs addition processing. With this addition, the reflection component of the echo signal from the direction corresponding to the reception directivity is enhanced, and a synthetic beam for ultrasonic transmission/reception is formed in accordance with the reception directivity and transmission directivity.

The B mode processing unit 15 receives the echo signal from the ultrasonic reception unit 13, and performs logarithmic amplification, envelope detection processing, and the like, thereby generating data whose signal strength is represented by a brightness level. This data is transmitted to the image generating unit 23 and is displayed as a B mode image representing the strength of a reflected wave as a brightness on the monitor 27.

A Doppler processing unit 16 frequency-analyzes velocity information from the echo signal received from the ultrasonic reception unit 13 to extract a blood flow, tissue, and contrast medium echo component by the Doppler effect, and obtains blood flow information such as an average velocity, variance, and power at multiple points.

The resolution optimization unit 17 executes processing (resolution optimization processing) based on a resolution optimization function (to be described later) under the control of the control processor 29.

Figure 2:
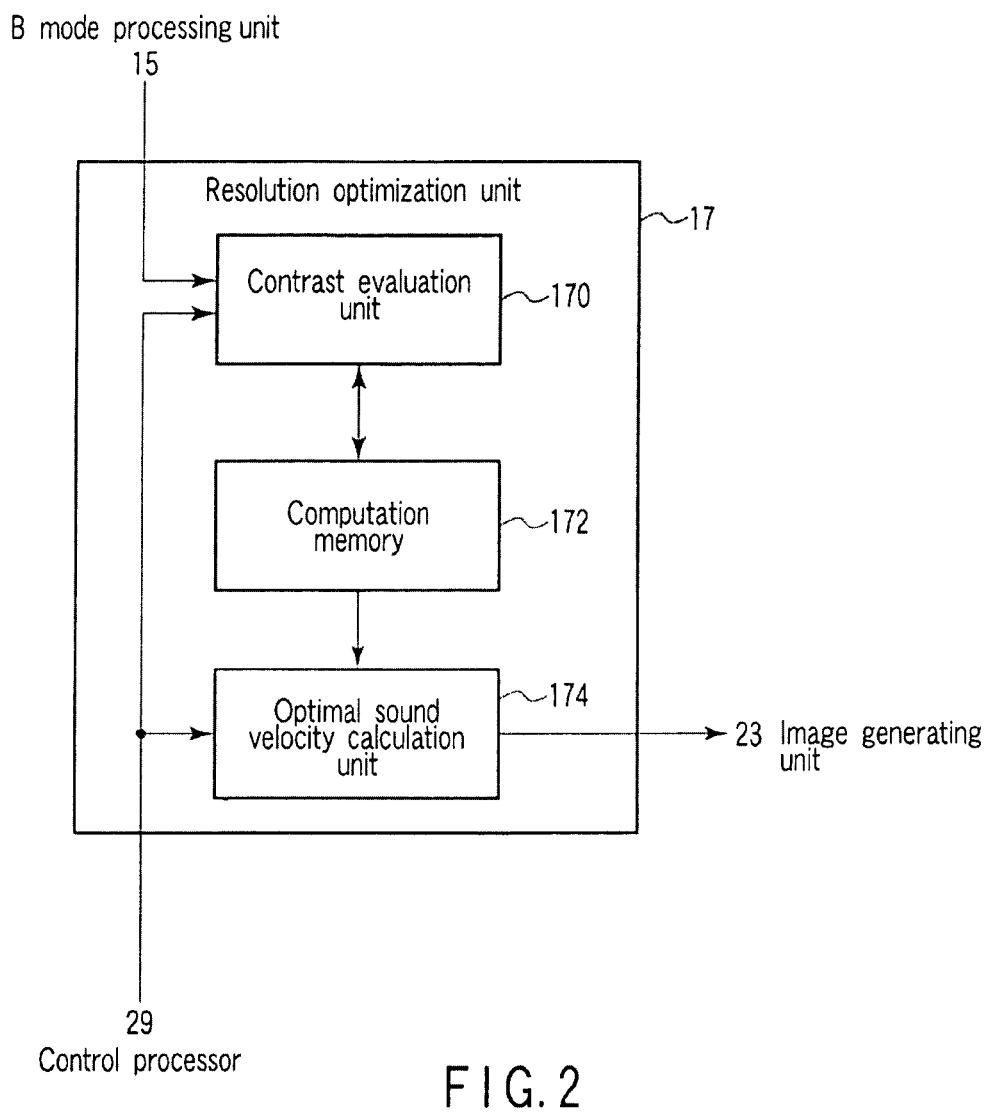
FIG. 2 is a block diagram showing an example of the arrangement of a resolution optimization unit 17.

FIG. 2 is a block diagram showing an example of the arrangement of the resolution optimization unit 17. Referring to FIG. 2, the resolution optimization unit 17 includes a contrast evaluation unit 170, a computation memory 172, and an optimal sound velocity calculation unit 174.

The contrast evaluation unit 170 uses the amplitude value at each position in a predetermined area (or the luminance value of each pixel) to, for example, evaluate contrast information about the area and generate a contrast value distribution map.

The computation memory 172 stores the contrast value distribution map and the like acquired by the contrast evaluation unit 170 and the optimal sound velocity map and the like acquired by the optimal sound velocity calculation unit 174.

The optimal sound velocity calculation unit 174, for example, calculates an optimal velocity and generates an optimal sound velocity map for each predetermined area, each depth, each visualization target slice, or the like on the basis of the contrast value distribution acquired by the contrast evaluation unit 170.

The image generating unit 23 generates an ultrasonic diagnosis image as a display image on the basis of various data received from the B mode processing unit 15 and Doppler processing unit 16. Note that data before it is input to the image generating unit 23 is sometimes called "raw data".

The image combining unit 25 combines the image received from the image generating unit 23 with character information of various types of parameters, scale marks, and the like, and outputs the resultant signal as a video signal to the monitor 27.

The monitor 27 displays morphological information (B mode image) in the living body, blood flow information (an average velocity image, variance image, power image, or the like) in the living body, various types of map images obtained by resolution optimization processing (to be described later), and the like in predetermined forms on the basis of video signals from the image combining unit 25.

The control processor 29 has a function as an information processing apparatus (computer) and controls the overall operation of this ultrasonic diagnosis apparatus. The control processor 29 reads out a dedicated program for implementing the resolution optimization function and control programs for executing a predetermined scan sequence, image generation/display, and the like from the storage unit 35, maps them in its internal memory, and executes computation/control and the like associated with various types of processing.

The interface unit 31 is an interface associated with the input unit 33, a network, and a new external storage device (not shown). The interface unit 31 can transfer data such as ultrasonic images, analysis results, and the like obtained by this apparatus to another apparatus through a network.

The input unit 33 has various types of switches, buttons, a trackball, a mouse, a keyboard, and the like which are used to input, to the ultrasonic diagnosis apparatus 1, various types of instructions and conditions, an instruction to set a region of interest (ROI), various types of image quality condition setting instructions, and the like from an operator. When, for example, the operator operates the end button or FREEZE button of the input unit 33, the transmission/reception of ultrasonic waves is terminated, and the ultrasonic diagnosis apparatus is set in a temporary stop state.

In addition, the input unit 33 includes switches and the like for issuing an instruction to start resolution optimization processing and setting/changing the initially set sound velocity in this processing, the optimal sound velocity calculation technique, and the like.

The storage unit 35 comprises recording media such as magnetic disks (floppy (registered trademark) disks, hard disks, and the like), optical disks (CD-ROMs, DVDs, and the like), and semiconductor memories, and a device which reads out information recorded on the media. The storage unit 35 stores transmission/reception conditions, a predetermined scan sequence, a program for executing the resolution optimization function, a control program for executing image generation/display processing, diagnosis information (a patient ID, findings by a doctor, and the like), a diagnosis protocol, a body mark generation program, various types of signal data, image data, and other data. Data in the storage unit 35 can be transferred to an external peripheral apparatus through the interface unit 31.

(Resolution Optimization Function)

The resolution optimization function which the ultrasonic diagnosis apparatus 1 has will be described next. This function determines an optimal sound velocity corresponding to a tissue component at each position within a scan slice, and calculates a reception delay time for each reception beam from each position within the scan slice by using the optimal sound velocity. The reception delay time (optimal reception delay time) calculated by using an optimal sound velocity is used to execute delay addition (phased addition) processing in a scan (real scan) for acquiring an ultrasonic image actually used for diagnosis. This corrects the difference between the sound velocity used for the calculation of a reception delay time and the actual sound velocity of propagation in the subject, thereby acquiring an ultrasonic image with optimized resolution.

For a concrete description of this embodiment, the resolution optimization function using image data after processing in the image generating unit 23 (i.e., data indicating a luminance value at each position on a slice, which is obtained through scan conversion processing) will be described. However, this resolution optimization function is not limited to this, and may be configured to use raw data before processing in the image generating unit 23 (i.e., data indicating an amplitude value at each position on a slice, which is obtained before scan conversion processing).

Figure 3:
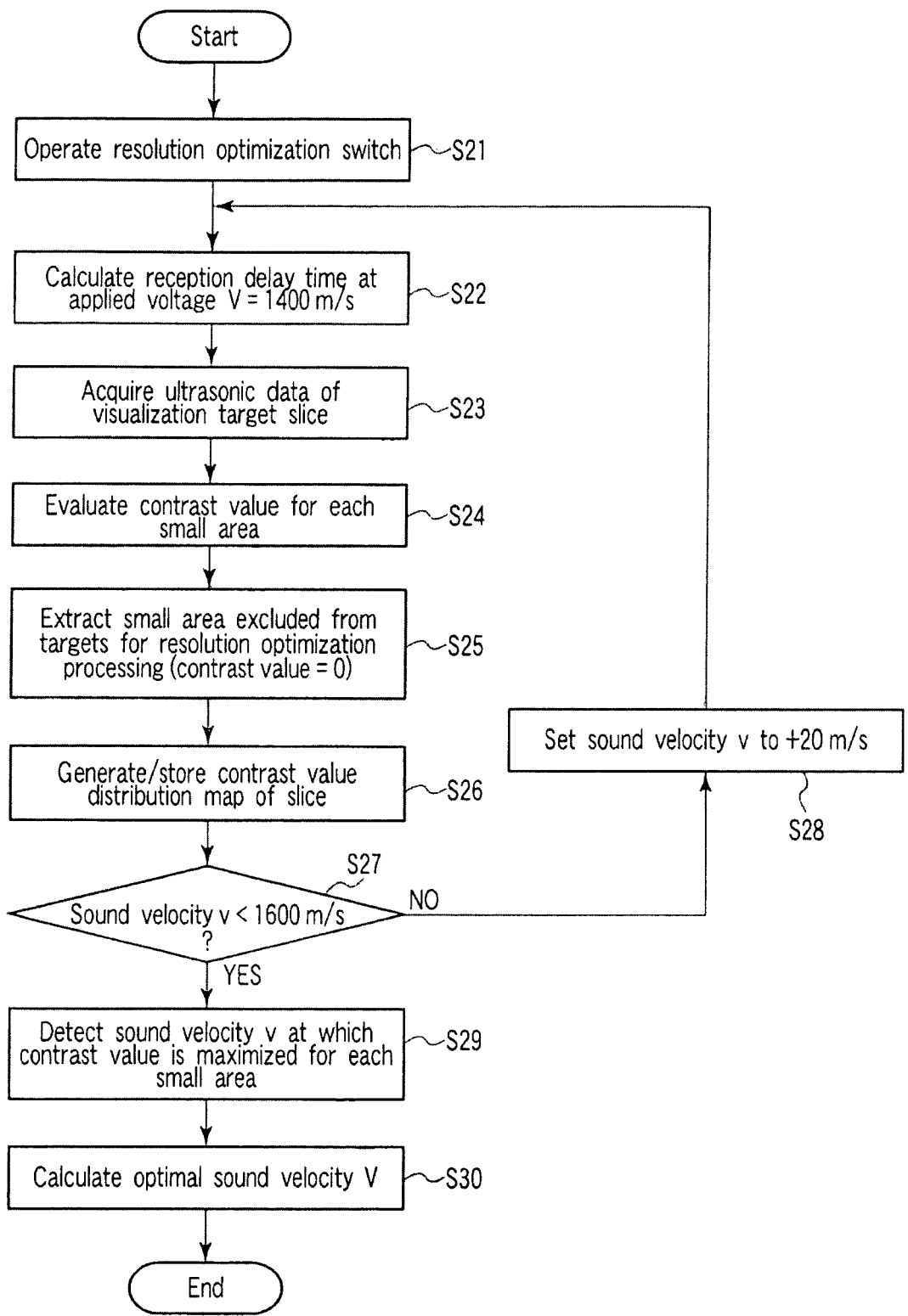
FIG. 3 is a flowchart showing the sequence of processing (resolution optimization processing) based on a resolution optimization function.

FIG. 3 is a flowchart showing a processing sequence based on the resolution optimization function. Referring to FIG. 3, first of all, when the operator issues an instruction to start resolution optimization processing by operating the resolution optimization switch of the input unit 33 or the like, the control processor 29 sets a sound velocity v to an initial value (e.g., v=1400 m/s) (step S21), and calculates a delay time at each position in one frame (i.e., a two-dimensional scan plane) (step S22).

The control processor 29 then two-dimensionally scans a visualization target slice, and executes delay addition by using the delay times calculated in step S22, thereby acquiring raw data or image data corresponding to one or a few frames associated with the visualization target slice (step S23). For a concrete description, assume that image data corresponding to one frame is acquired in step S23.

The contrast evaluation unit 170 segments the image data associated with the visualization target slice into m×n small areas like those shown in FIG. 4, and evaluates a contrast value for each small area (step S24). In this case, the evaluation method to be used for contrast values is not specifically limited. For example, the contrast evaluation unit 170 can calculate the variance of luminance values existing in each area (the variance of amplitudes in the case of raw data), the difference value or slope value between the maximum and minimum values of luminances in each area (the difference value between the maximum and minimum values of amplitudes in the case of raw data), and a differential value (a first-order differential value or second-order differential value), and directly or indirectly evaluate contrast values by using the calculated values. For a concrete description, assume that in this embodiment, a contrast value in each area is evaluated by the variance or differential value of luminance values existing in each area.

The resolution optimization unit 17 extracts some of the small areas constituting the visualization target slice which are excluded from this resolution optimization processing on the basis of the obtained variances (step S25). More specifically, the resolution optimization unit 17 determines whether a given variance value falls within a predetermined range having a lower limit α and an upper limit β. If the variance value falls outside the predetermined range, contrast value=0 is set in the small area corresponding to the variance value.

The contrast evaluation unit 170 then generates a contrast value distribution map indicating the distribution of contrast values Vmn in the respective small areas in the visualization target slice, as shown in, for example, FIG. 5. The computation memory 172 stores the generated contrast value distribution map in correspondence with set sound velocity information (step S26).

The control processor 29 determines whether the current sound velocity v exceeds a predetermined upper limit value (e.g., 1,600 m/s) (step S27). If the current sound velocity v exceeds the upper limit value, the process shifts to step S29.

If the current sound velocity v does not exceed the predetermined upper limit value, the value obtained by adding, for example, +20 m/s to the current sound velocity v is set as a new sound velocity v. The respective processes in steps S22 to S27 are repeated in the same manner as described above (step S28). With this operation, a contrast value distribution map is generated for each sound velocity (in this case, for each sound velocity at 20 m/s intervals in the range of 1,400 m/s to 1,600 m/s), and is stored in the computation memory 172.

The optimal sound velocity calculation unit 174 determines, for each small area, a sound velocity at which the contrast value is maximized (step S29).

Figure 6:
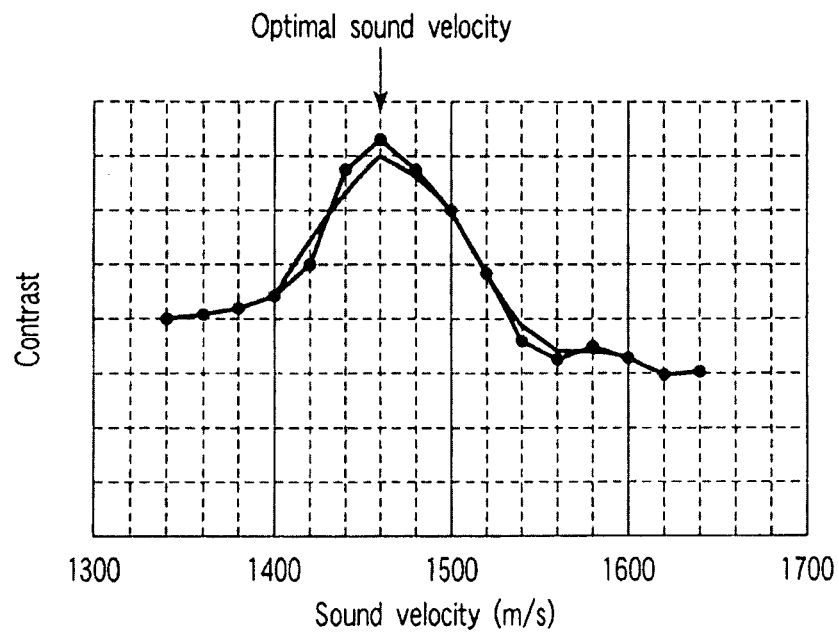
FIG. 6 is a graph for explaining an example of determination processing for a sound velocity at which the contrast value is maximized in each small area.

FIG. 6 is a graph for explaining an example of determination processing for a sound velocity at which the contrast value is maximized. The optimal sound velocity calculation unit 174 plots the relationship between the contrast value and the sound velocity, as shown in, for example, FIG. 6. The optimal sound velocity calculation unit 174 calculates a regression curve associated with each plotted point, and determines a sound velocity vmax at which the contrast value is maximized, on the basis of the regression curve.

The optimal sound velocity calculation unit 174 then calculates an optimal sound velocity V by using the sound velocity vmax at which the contrast value in each small area is maximized (step S30). Various techniques can be used to calculate an optimal sound velocity V. Several techniques will be described according to the examples.

EXAMPLE 1

First of all, with regard to a small area in which contrast value=0 is not set in step S26, a sound velocity vmax at which the contrast value is maximized is set as the optimal sound velocity V in the small area. With regard to a small area in which contrast value=0 is set, the optimal sound velocity V is calculated by interpolation using a preset sound velocity or the optimal sound velocities in a plurality of neighboring small areas. As a result of this calculation, an optimal sound velocity map for each small area on the slice can be obtained, as shown in, for example, FIG. 7.

EXAMPLE 2

Example 1 has exemplified the case in which an optimal sound velocity is calculated and set for each small area. In contrast to this, Example 2 exemplifies a case in which an optimal velocity is calculated and set for each depth.

Figure 7:
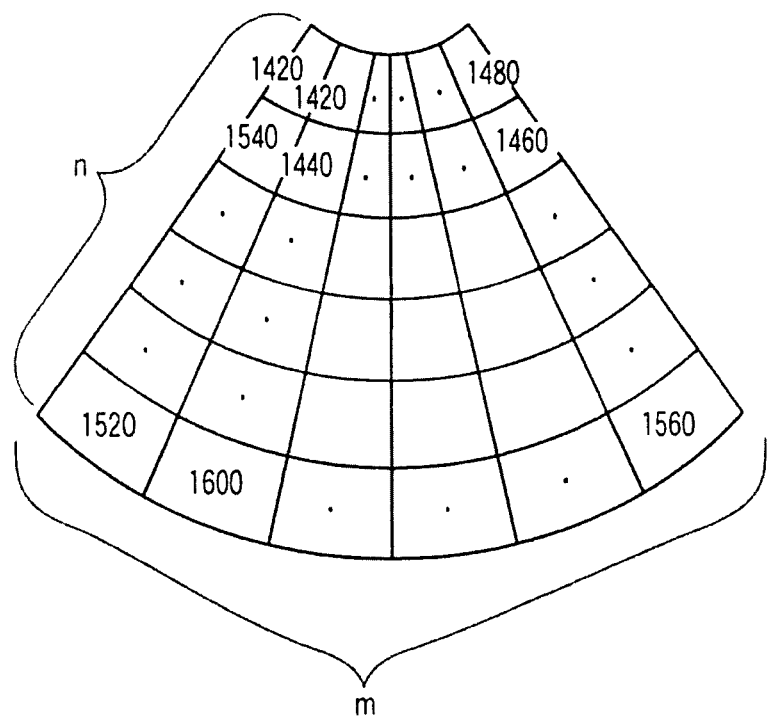
FIG. 7 is a view showing an example of an optimal sound velocity map for each small area which is obtained by resolution optimization processing.

An optimal sound velocity calculation unit 174 calculates the average value of the optimal sound velocities in a plurality of small areas belonging to the same depth from the ultrasonic wave application surface (or the body surface of the subject) on the optimal sound velocity map for each small area shown in, for example, FIG. 7, and sets the average value as a small area optimal sound velocity belonging to the depth. As a result of this calculation, an optimal sound velocity map for each depth on the slice can be obtained as shown in, for example, FIG. 8.

EXAMPLE 3

Example 3 exemplifies a case in which one optimal velocity is set for the visualization target slice.

Figure 8:
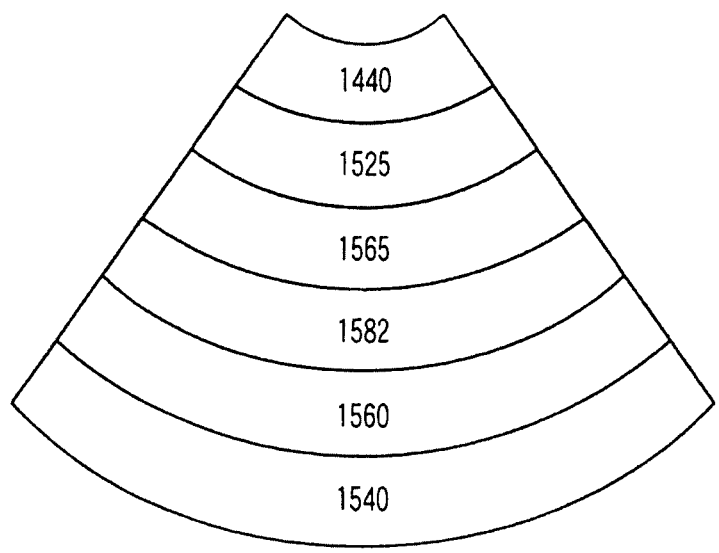
FIG. 8 is a view showing an example of an optimal sound velocity map for each depth which is obtained by resolution optimization processing.
Figure 9:
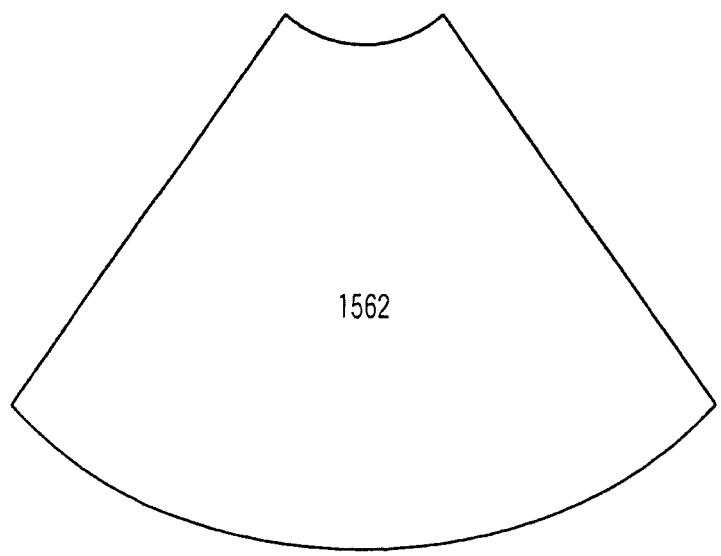
FIG. 9 is a view showing an example of an optimal sound velocity map on a visualization target slice which is obtained by resolution optimization processing.

An optimal sound velocity calculation unit 174 calculates the average value of the optimal sound velocities in all the small areas or the average value of the optimal sound velocities at all the depths on the optimal sound velocity map for each small area shown in FIG. 7 or the optimal sound velocity map for each depth shown in FIG. 8, and sets the average value as an optimal sound velocity associated with the visualization target slice. As a result of this calculation, one optimal sound velocity map is obtained for the visualization target slice as shown in, for example, FIG. 9.

It is possible to arbitrarily select one of the above techniques. In addition, it suffices to analyze the distribution state of optimal sound velocities in the respective small areas and automatically select one of the techniques on the basis of the analysis result.

Note that a sound velocity has a correlation only with an azimuth resolution (a resolution in the horizontal direction), and hence evaluation including a distance resolution (a resolution in the time direction) with no correlation may degrade the accuracy. It is therefore preferable to limit the evaluation of a contrast value to the horizontal direction (the direction perpendicular to a scanning line). That is, an average value or maximum value in the time direction is obtained from contrast values in each small area which are evaluated at each depth, and is set as an optimal velocity for each small area. This can implement the optimization of resolutions with high accuracy.

(Operation)

The operation of an ultrasonic diagnosis apparatus 1 when performing a real scan using the resolution optimization function will be described next.

Figure 10:
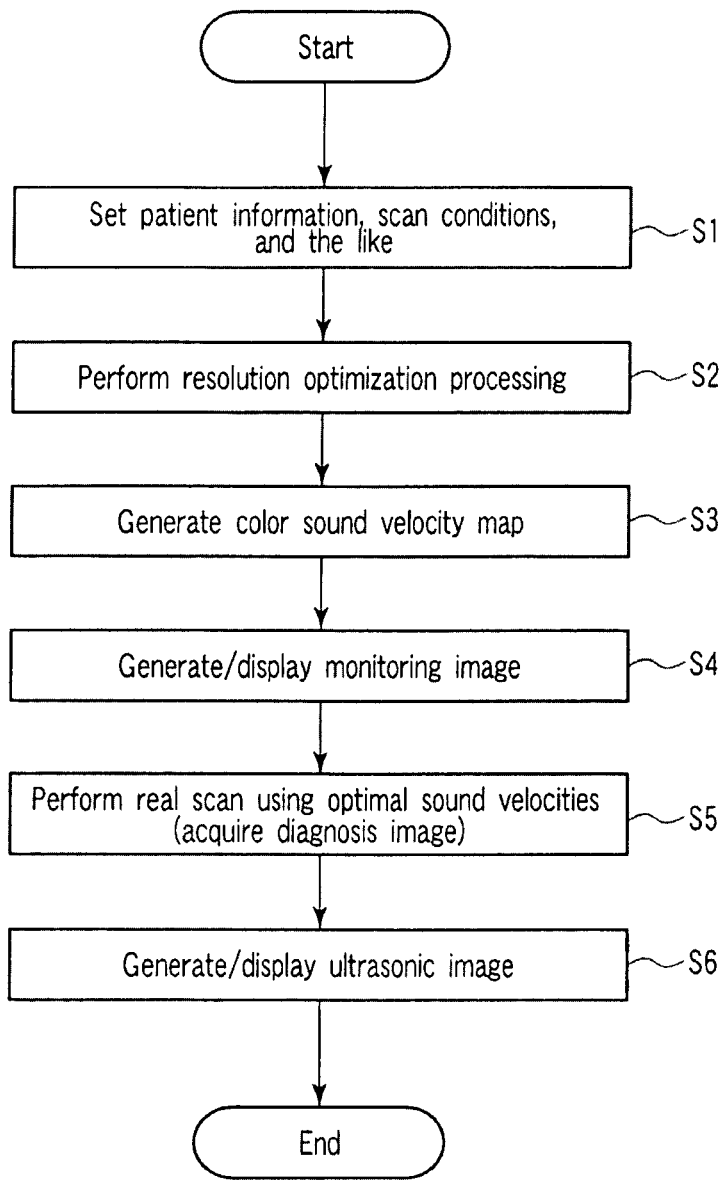
FIG. 10 is a flowchart showing each processing sequence when a real scan is performed by using a resolution optimization function.

FIG. 10 is a flowchart showing each processing sequence when a real scan is performed by using the resolution optimization function. As shown in FIG. 10, first of all, when patient information, scan conditions, and the like are input through an input unit 33 (step S1), a control processor 29 executes the above resolution optimization processing in response to the operation of the resolution optimization switch (step S2).

An image generating unit 23 then generates a color sound velocity map by using the optimal sound velocity map for each small area which is obtained by the resolution optimization processing (step S3).

In this case, a color sound velocity map indicates the distribution of optimal sound velocities in the form of a color distribution by assigning predetermined colors to the respective small areas (used in the resolution optimization processing) constituting a visualization target slice in accordance with the values of optimal sound velocities. Note that the sound velocity changes depending on the components of a propagation medium. That is, the color sound velocity map allows the operator to visually recognize the distribution of the tissue components of a visualization target slice by colors.

As shown in FIG. 11, this color sound velocity map is displayed together with a B mode image associated with the visualization target slice which is acquired in real time (or acquired in resolution optimization processing) and color bars indicating the correspondence between optimal sound velocities and colors (step S4). Assume that the operator observes the color sound velocity map and finds various colors are scattered and distributed on the map. In this case, the optimal velocities obtained by the technique according to the first embodiment can be set. If color changes almost in accordance with changes in depth on the color sound velocity map, the optimal velocities obtained by the technique according to the second embodiment can be set. In addition, if similar colors are in large amount on the color sound velocity map, the optimal velocity obtained by the technique according to the third embodiment may be set.

The control processor 29 then executes a real scan by using the optimal velocity or velocities (step S5). In this case, if the optimal velocities are set in the form shown in, for example, FIG. 7, the control processor 29 executes delay addition processing by using the delay times calculated by using the set optimal velocities. If the optimal velocities are set in the form shown in, for example, FIG. 8, the control processor 29 executes delay addition processing by using the delay times calculated by using the set optimal velocities is in accordance with the respective depths. If the optimal velocity is set in the form shown in, for example, FIG. 9, the control processor 29 newly calculates a delay time by using the optimal velocity and executes delay addition processing by using the delay time.

The ultrasonic image acquired by this real scan is displayed on the monitor 27 in a predetermined form (step S6).

(Effect)

According to the above arrangements, the following effects can be obtained.

This ultrasonic diagnosis apparatus determines an optimal sound velocity corresponding to a tissue component at each position in a scan slice, and calculates a reception delay time or the like for each reception beam from each position in the scan slice by using the determined optimal sound velocity. Executing delay addition processing in a scan for acquiring an ultrasonic image actually used for diagnosis by using the reception delay time calculated by using an optimal sound velocity in this manner makes it possible to correct the difference between the set sound velocity used for the calculation of a reception delay time and the actual in vivo sound velocity and acquire an ultrasonic image with optimized resolution.

In the case in which differential values are used as contrast values, in particular, edges in the respective small areas can be actively extracted, and hence this technique is preferable for the implementation of optimization of a resolution. That is, if an average value or a variance value is used, an evaluation result may be influenced by the position of an ROI set for the calculation of a variation. If a frequency is used as a contrast value, a large amount of data are required for frequency analysis. This will degrade the real-time performance, and increase the apparatus size and cost. In contrast to these cases, using differential values as contrast values can more preferably acquire an ultrasonic image with optimized resolution easily at a low cost.

Figure 12:
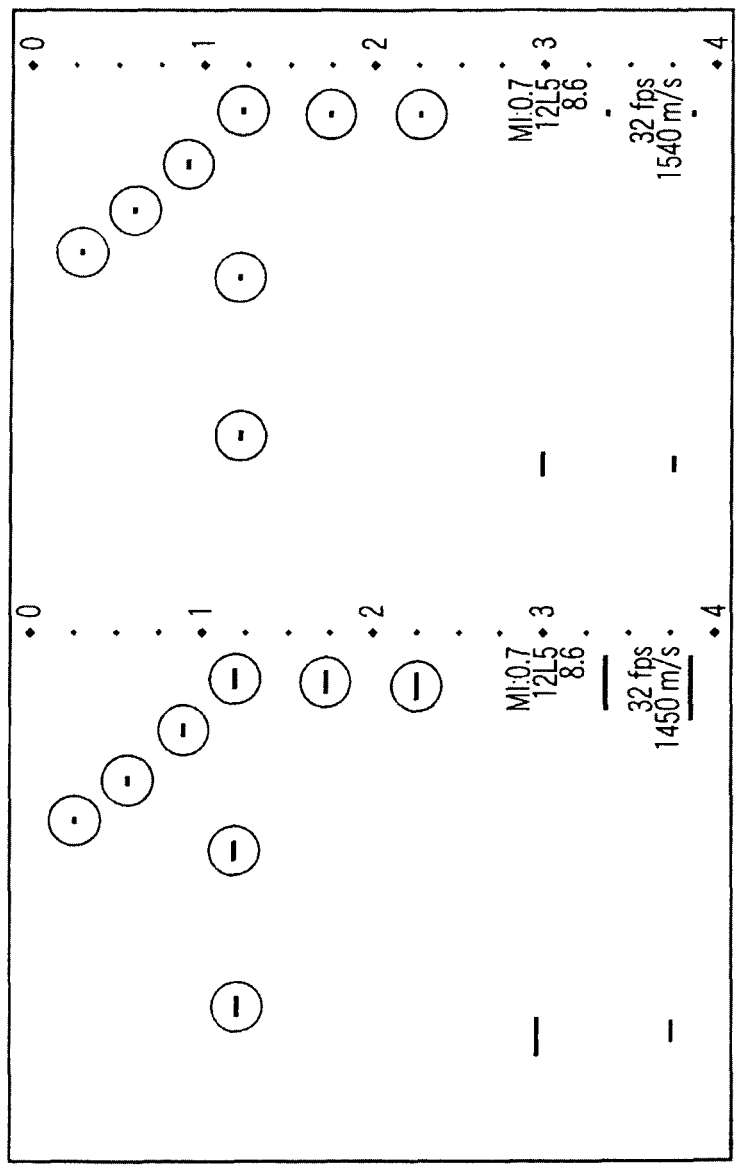
FIG. 12 are a view exemplarily showing an ultrasonic image (a) obtained by a conventional technique, and a view exemplarily showing an ultrasonic image (b) acquired by correcting the difference between the set sound velocity used for the calculation of a reception delay time and the actual in vivo sound velocity.
Figure 13:
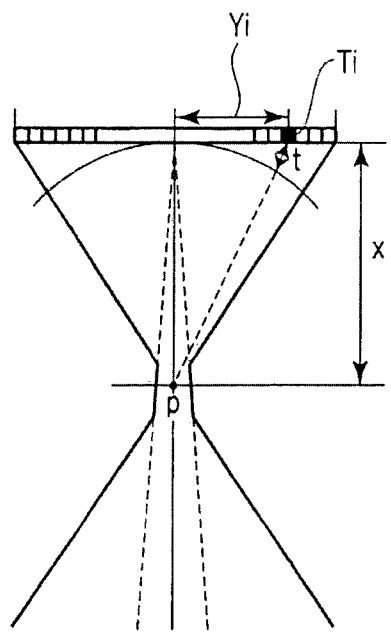
FIG. 13 is a view for explaining a reception delay time calculation technique.
Figure 14:
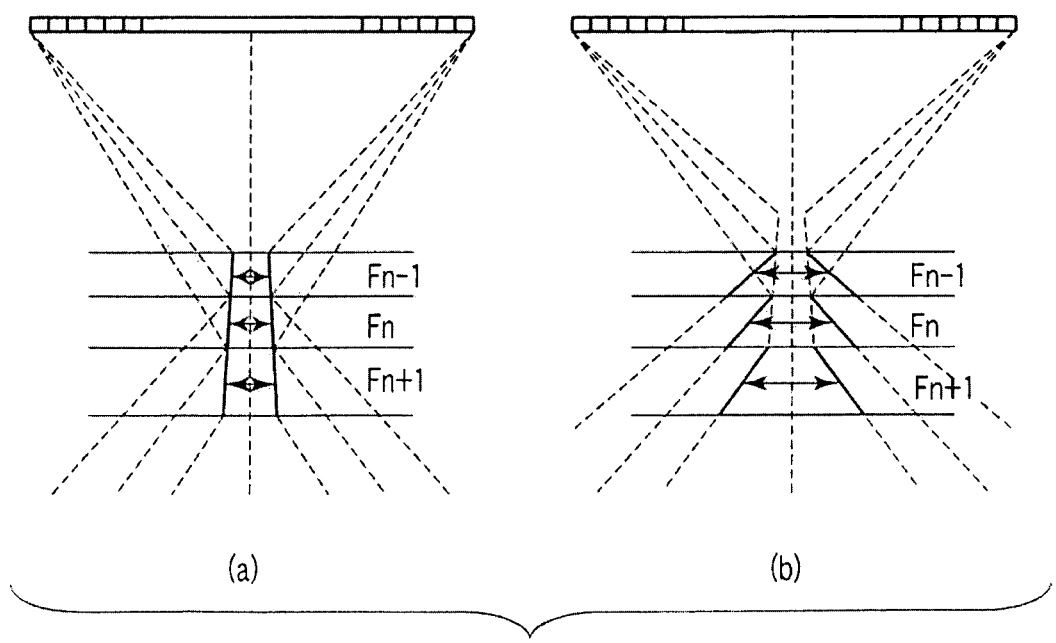
FIG. 14 is a view for explaining convergence line shifts due to sound velocity differences.

FIG. 12 is a view exemplarily showing an ultrasonic image (a) obtained by the conventional technique (i.e., an ultrasonic image acquired without any correction of the difference between the set sound velocity used for the calculation of a reception delay time and the actual in vivo sound velocity). FIG. 12 is a view exemplarily showing an ultrasonic image (b) acquired by correcting the difference between the set sound velocity used for the calculation of a reception delay time and the actual in vivo sound velocity by this resolution optimization processing. A comparison between the two ultrasonic images (a) and (b) will reveal that the targets within the circular frames in the ultrasonic images (b) are visualized with higher resolution as compared with the targets within the circular frames in the ultrasonic images (a).

In addition, this ultrasonic diagnosis apparatus can generate and display a color sound velocity map by resolution optimization processing. The operator can therefore visually recognize the structure of the visualization target slice and the distribution of components from the viewpoint of velocity by using the color sound velocity map. In addition, a calculation technique for optimal sound velocities can be selected on the basis of the observation result on the color sound velocity map.

The present invention is not limited to the above embodiment, and constituent elements can be modified and embodied in the execution stage within the spirit and scope of the invention. The following are concrete modifications.

(1) Each function according to the embodiment can also be implemented by installing programs for executing the corresponding processing in a computer such as a workstation and unarchiving them in a memory. In this case, the programs which can cause the computer to execute the corresponding techniques can be distributed by being stored in recording media such as magnetic disks (floppy (registered trademark) disks, hard disks, and the like), optical disks (CD-ROMs, DVDs, and the like), and semiconductor memories.

(2) In the above embodiment, the size of each small area is not specifically limited. If, for example, each small area is set as an area for each depth as shown in FIG. 8, acquiring an optimal sound velocity for each small area is equivalent to acquiring an optimal sound velocity for each depth. In addition, making small areas correspond to the respective pixels can acquire optimal velocities unique to all the points on a visualization target slice.

(3) The above embodiment has exemplified the case in which a visualization target is a slice. However, the present invention is not limited to this. This resolution optimization function can also be used even when a three-dimensional area is to be visualized. In such a case, it suffices to perform the above resolution optimization processing for each of slices constituting a three-dimensional area as a visualization target or segment a three-dimensional area as a visualization target into small three-dimensional areas and perform the above resolution optimization processing for each small area.

In addition, various inventions can be formed by proper combinations of a plurality of constituent elements disclosed in the above embodiments. For example, several constituent elements may be omitted from all the constituent elements disclosed in the above embodiment. Furthermore, constituent elements in different embodiments may be properly combined.

What is claimed is:

1. An ultrasonic imaging apparatus comprising:
   a storage device which stores a plurality of ultrasonic data acquired by using reception delay addition processing, based on different sound velocities, for a visualization target slice of a subject;
   a computer configured to operate as:
   a contrast value acquisition unit which segments the target slice into a plurality of small areas and acquires contrast values which correspond to different sound velocities, in each small area by using the plurality of ultrasonic data; and
   a determination unit which determines at least one of sound velocities in execution of ultrasonic scans on the visualization target slice by using a contrast value for each of different sound velocities for said each small area.

2. An apparatus according to claim 1, wherein the contrast values corresponding to the different sound velocities are differential values of amplitude values or differential values of luminance values in each small area.

3. An apparatus according to claim 2, wherein the contrast values corresponding to the different sound velocities are variance values of amplitude values or variance values of luminance values in each small area.

4. An apparatus according to claim 1, wherein the contrast values are difference values between a maximum value and a minimum of an amplitude for each different sound velocity or difference values between a maximum value and a minimum of a luminance for each different sound velocity in each small area.

5. An apparatus according to claim 1, wherein the determination unit determines a maximum sound velocity in said each small area which maximizes a contrast value as the sound velocity when an ultrasonic scan is performed on the visualization target slice.

6. An apparatus according to claim 1, wherein the determination unit determines a maximum sound velocity in said each small area which maximizes a contrast value, and determines an average velocity for each depth, which is obtained by using a maximum sound velocity in said each small area, as the sound velocity when an ultrasonic scan is performed on the visualization target slice.

7. An apparatus according to claim 1, wherein the determination unit determines a maximum sound velocity in said each small area which maximizes a contrast value, and determines an average velocity on the visualization target slice, which is obtained by using a maximum sound velocity in said each small area, as the sound velocity when an ultrasonic scan is performed on the visualization target slice.

8. An apparatus according to claim 1, further comprising:
   the computer to be configured to operate as a map generating unit which generates a color velocity map by assigning a predetermined color to said each small area in accordance with a maximum sound velocity which maximizes a contrast value; and
   a display device which displays the color velocity map in a predetermined form.

9. An apparatus according to claim 1, further comprising an ultrasonic reception unit which performs reception delay addition for an echo signal, which is received by each ultrasonic transducer by ultrasonic transmission/reception, by using the optimal velocity.

10. An apparatus according to claim 1, wherein the contrast value acquisition unit segments said plurality of ultrasonic data into said plurality of small areas along a horizontal direction which is a direction perpendicular to an ultrasonic scanning line, and acquires a contrast value for said each sound velocity for each depth corresponding to said each small area.

11. An apparatus according to claim 1, wherein the sound velocities in execution of ultrasonic scans on the visualization target slice are optimal velocities.

12. An ultrasonic velocity optimization method comprising:
   segmenting a visualization target slice of a subject into a plurality of small areas;
   acquiring a contrast value which correspond to different sound velocities, in said each small area by using a plurality of ultrasonic data acquired by using reception delay addition processing for the visualization target slice of the subject on the basis of different sound velocities; and
   determining at least one of sound velocities in execution of ultrasonic scans on the visualization target slice by using the contrast values for each of different sound velocities for said each small area.

13. A method according to claim 12, wherein the contrast values corresponding to the different sound velocities are differential values of amplitude values or differential values of luminance values in each small area.

14. A method according to claim 13, wherein the contrast values corresponding to the different sound velocities are variance values of amplitude values or variance values of luminance values in each small area.

15. A method according to claim 12, wherein the contrast values are difference values between a maximum value and a minimum of an amplitude for each different sound velocity or difference values between a maximum value and a minimum of a luminance for each different sound velocity in each small area.

16. A method apparatus according to claim 12, wherein in determining, a maximum sound velocity in said each small area which maximizes a contrast value is determined as the sound velocity when an ultrasonic scan is performed on the visualization target slice.

17. A method according to claim 12, wherein in the determining, a maximum sound velocity is determined in said each small area which maximizes a contrast value, and an average velocity for each depth which is obtained by using a maximum sound velocity in said each small area is determined as the sound velocity when an ultrasonic scan is performed on the visualization target slice.

18. A method according to claim 12, wherein in the determining, a maximum sound velocity in said each small area which maximizes a contrast value is determined, and an average velocity on the visualization target slice which is obtained by using a maximum sound velocity in said each small area is determined as the sound velocity when an ultrasonic scan is performed on the visualization target slice.

19. A method according to claim 12, further comprising:
generating a color velocity map by assigning a predetermined color to said each small area in accordance with a maximum sound velocity which maximizes a contrast value; and
displaying the color velocity map in a predetermined form.

20. A method according to claim 12, further comprising performing reception delay addition for an echo signal, which is received by each ultrasonic transducer by ultrasonic transmission/reception, by using the optimal velocities.

21. A method according to claim 12, wherein in acquiring a contrast value, said plurality of ultrasonic data are segmented into said plurality of small areas along a horizontal direction which is a direction perpendicular to an ultrasonic scanning line, and a contrast value is acquired for each of said sound velocities for each depth corresponding to said each small area.

22. A method according to claim 12, wherein the sound velocities in execution of ultrasonic scans on the visualization target slice are optimal velocities.

23. An ultrasonic imaging apparatus comprising:
a storage device which stores a plurality of ultrasonic data acquired by using reception delay addition processing, based on different sound velocities, for a visualization target slice of a subject;
a computer configured to operate as:
a contrast value acquisition unit which segments the target slice into a plurality of small areas and selects a small area form the plurality of small areas based on variance values or luminance values in each small area;
a calculation unit which calculates a contrast value in the selected small area; and
a determination unit which determines at least one of sound velocities in execution of ultrasonic scans on the visualization target slice by using the contrast value.

24. An apparatus according to claim 23, wherein the contrast value is differential values of amplitude values or differential values of luminance values in the selected small area.

25. An apparatus according to claim 23, wherein the contrast value is differential values of amplitude values or differential values of luminance values in the selected small area.

26. An ultrasonic imaging apparatus comprising:
a storage device which stores a plurality of ultrasonic data acquired by using reception delay addition processing, based on different sound velocities, for a visualization target slice of a subject;
a computer configured to operate as:
a contrast value acquisition unit which segments the target slice into a plurality of small areas and selects a small area form the plurality of small areas based on variance values of amplitude values or of luminance values in each small area;
a calculation unit which calculates a contrast value in the selected small area; and
a determination unit which determines at least one of sound velocities in execution of ultrasonic scans on the visualization target slice by using the contrast value.

* * * * *

UNITED STATES PATENT AND TRADEMARK OFFICE
CERTIFICATE OF CORRECTION

PATENT NO. : 8,926,512 B2
APPLICATION NO. : 12/056596
DATED : January 6, 2015
INVENTOR(S) : Akihiro Kakee It is certified that error appears in the above-identified patent and that said Letters Patent is hereby corrected as shown below:

On the title page item (73), Second Assignee's city is spelled incorrectly. Item (73) should read:

-- (73) Assignees: Kabushiki Kaisha Toshiba, Tokyo (JP);
Toshiba Medical Systems Corporation, Otawara-shi (JP) --

Signed and Sealed this
Twenty-first Day of April, 2015

Michelle K. Lee
*Director of the United States Patent and Trademark Office*